United States Patent [19]
Fujita

[11] Patent Number: 5,432,698
[45] Date of Patent: Jul. 11, 1995

[54] DATA INPUT AND OUTPUT CONTROLLER FOR ANESTHESIA MONITORING SYSTEM

[75] Inventor: Michio Fujita, Philadelphia, Pa.

[73] Assignee: Modular Instruments, Inc., Malvern, Pa.

[21] Appl. No.: 251,541

[22] Filed: May 31, 1994

[51] Int. Cl.⁶ .......................................... G06F 159/00
[52] U.S. Cl. ............................................... 364/413.02
[58] Field of Search .................... 364/413.01, 413.02, 364/413.03; 395/275

[56] References Cited

U.S. PATENT DOCUMENTS

| | | | |
|---|---|---|---|
| H696 | 10/1989 | Davidson | 364/900 |
| 4,435,781 | 3/1984 | Stattel et al. | 364/900 |
| 4,509,113 | 4/1985 | Heath | 364/200 |
| 4,638,422 | 1/1987 | Rees | 364/200 |
| 4,695,955 | 9/1987 | Faisandier | 364/413.03 |
| 4,760,330 | 7/1988 | Lias, Jr. | 371/15.1 |
| 4,920,511 | 4/1990 | Brier et al. | 364/900 |
| 5,216,597 | 6/1993 | Beckers | 364/413.02 |
| 5,243,699 | 9/1993 | Nickolls et al. | 395/275 |
| 5,307,463 | 4/1994 | Hyatt et al. | 395/275 |
| 5,331,549 | 7/1994 | Crawford, Jr. | 364/413.02 |
| 5,339,818 | 8/1994 | Baker et al. | 364/413.03 |

Primary Examiner—Donald E. McElheny, Jr.
Attorney, Agent, or Firm—Michael F. Petock

[57] ABSTRACT

Apparatus provides an interface between a computer, various data sources such as patient monitors and a printer via the parallel printer port of a computer for use in a data management system for anesthesia. Substantially any computer may be utilized by use of the parallel printer port to provide fast and efficient inputting of data to the computer, communication with monitors and other data sources and to enable the use of the printer via the parallel printer port. The patient's vital signs and data from other data sources is supplied to the computer via the status lines of the parallel printer port while the data lines are utilized to control a processor in the apparatus with the printer disabled by reason of the absence of a strobe pulse. The apparatus includes signal processing circuitry which multiplexes a number of analog data signals and converts them to digital signals for storage and transmission to the computer upon request. RS232 type signals are also converted to TTL signals for storage and transmission to the computer upon demand. Upon the computer providing the strobe pulse, printouts of data may be provided via the printer.

13 Claims, 4 Drawing Sheets

DATA INPUT AND OUTPUT CONTROLLER FOR ANESTHESIA MONITORING SYSTEM

FIELD OF THE INVENTION

The present invention relates to interface apparatus utilized in a patient data management system for anesthesia. More particularly, the present invention relates to apparatus utilized to interface inputs and outputs from a computer with patient monitors, other data sources and a printer.

BACKGROUND OF THE INVENTION

Whenever a patient is anaesthetized for a surgical or other procedure, there is a need to keep track of and record a significant amount of data. Further, this data needs to be updated regularly throughout the period during which the patient is anaesthetized. Some of this information may include blood pressure, electrocardiogram, and respiration data monitoring, lab results including blood pH, gases and electrolytes and various other information necessary and/or conventionally tracked and recorded during the period of anesthetization.

SUMMARY OF THE INVENTION

The present invention provides apparatus which enables various data sources such as blood pressure monitors and other patient monitors, lab reports and other data sources to be inputted to a computer, allows the computer to communicate with the data sources and/or to print on a printer substantially independent of the type of computer utilized, utilizing the parallel printer port of a computer which is available on substantially all computers.

The present invention enables substantially any one of a number of the various computers on the market to be utilized as the computer to be used in the patient data management system, as long as it has a parallel printer port, which is available on almost all computers. This solves the problem of variations in various computers and particularly the problem of rapid change in computer models. Further it solves the problem where there may be no available "slots" or data ports available for the multitude of inputs and outputs required for operation of the system. With the tendency to reduce the size of the computers, it is anticipated that this problem may become more serious in the future.

The present invention enables the use of a relatively fast parallel port for the inputting and outputting of data and other information, as contrasted to the possible use of a serial port. In the system as utilized, it is contemplated that one of the serial ports which may be available will be used for a touch screen device.

In accordance with the present invention, apparatus is provided which is intended for use primarily during anesthetization of a patient for inputting data to a computer utilized to monitor the patient's vital signs and other data which includes means for connecting to the parallel port of a computer, which means may preferably be a cable connected at one end to the parallel port of the computer and at the other end to a parallel port on the apparatus. Also provided is means for connecting to the parallel port of a printer, which in a preferred embodiment may be a cable connected to the parallel port of the printer and to a parallel port on the apparatus. The apparatus includes means responsive to signals generated by the computer for enabling the computer to print data or to enable the computer to receive data from a plurality of data sources which provide data relating to a patient's anesthetization.

More particularly, the apparatus of the present invention is utilized as a data interface between a computer and a plurality of patient monitors and other data sources relating to a patient undergoing anesthesia. The apparatus includes means for connecting to the parallel port of a computer and means for connecting to a plurality of patient monitors. The apparatus includes means responsive to signals generated by the computer. This means includes at least a processor, memory and signal processing means. The signal processing means includes circuitry for multiplexing a plurality of analog signals and converting them to digital signals for storage in the memory. The processor controls the storage of the signals in memory at appropriate addresses and retrieves selected stored signals from memory as called for by the computer and enables transmission of the signals to the computer.

The signal processing circuitry may further include circuitry for converting RS232 type or alternating signals to TTL or digital pulse signals conventionally utilized by the computer. A processor controls the storage and transmission of the TTL signals in memory and transmission to the computer in response to computer requests. The processor may further receive control signals via data lines from the computer for generating one or more signals for transmission to one or more patient monitors. The apparatus also may include means for connecting to the parallel port of a printer and means for controlling data flow whereby the printer may be enabled by a strobe pulse for printing and disabled by the absence of a strobe signal whereby data on the data lines is utilized to control the processor.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

DETAILED DESCRIPTION OF THE PREFERRED EMBODIMENTS

Figure 1:
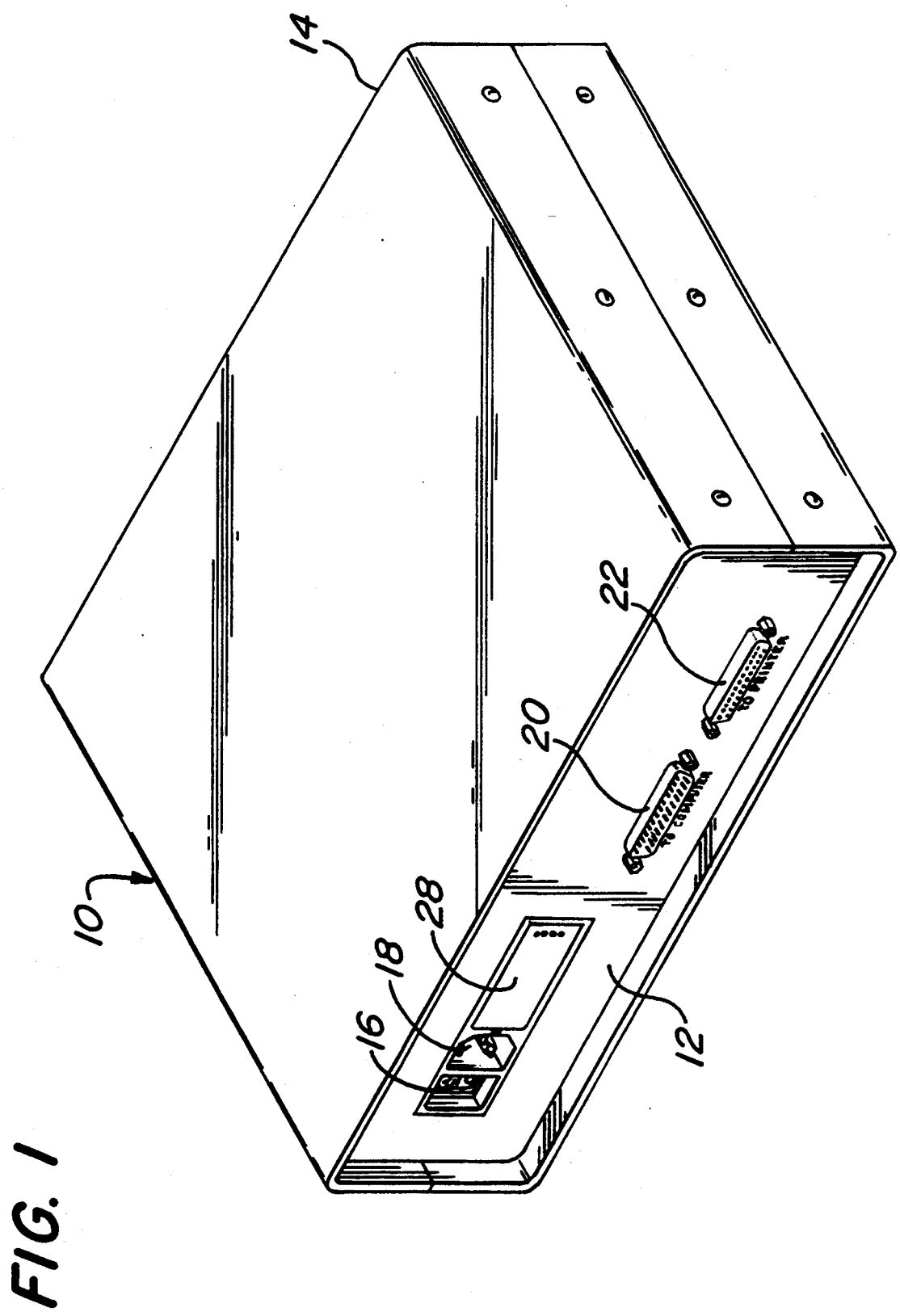
FIG. 1 is a view in perspective of an apparatus in accordance with the present invention, particularly illustrating on the back panel thereof, a pair of parallel ports, one being for connection to a computer and the other to a printer.

Referring now to the drawings, wherein like numerals indicate like elements, there is shown in FIG. 1 an apparatus 10 in accordance with the present invention which is structured and configured to function as a data input and output controller interface for a patient data management system which is particularly adapted for use in connection with anesthetized patients. Apparatus 10 is provided with a housing, including a back panel 12 and a front panel 14. Back panel 12 is provided with an on/off switch 16 and a power inlet jack 18. Back panel 12 also contains a fuse and alternating current voltage selection unit at 28. Back panel 12 is also provided with parallel ports 20 and 22. Parallel ports 20 and 22 are of the type normally utilized in connection with printers and are referred to herein as parallel printer ports. Parallel printer port 20 is intended to be connected to the parallel printer port of a computer and is accordingly marked "to computer". Parallel port 22 is intended to be connected to the parallel port of a printer and is marked "to printer".

Figure 2:
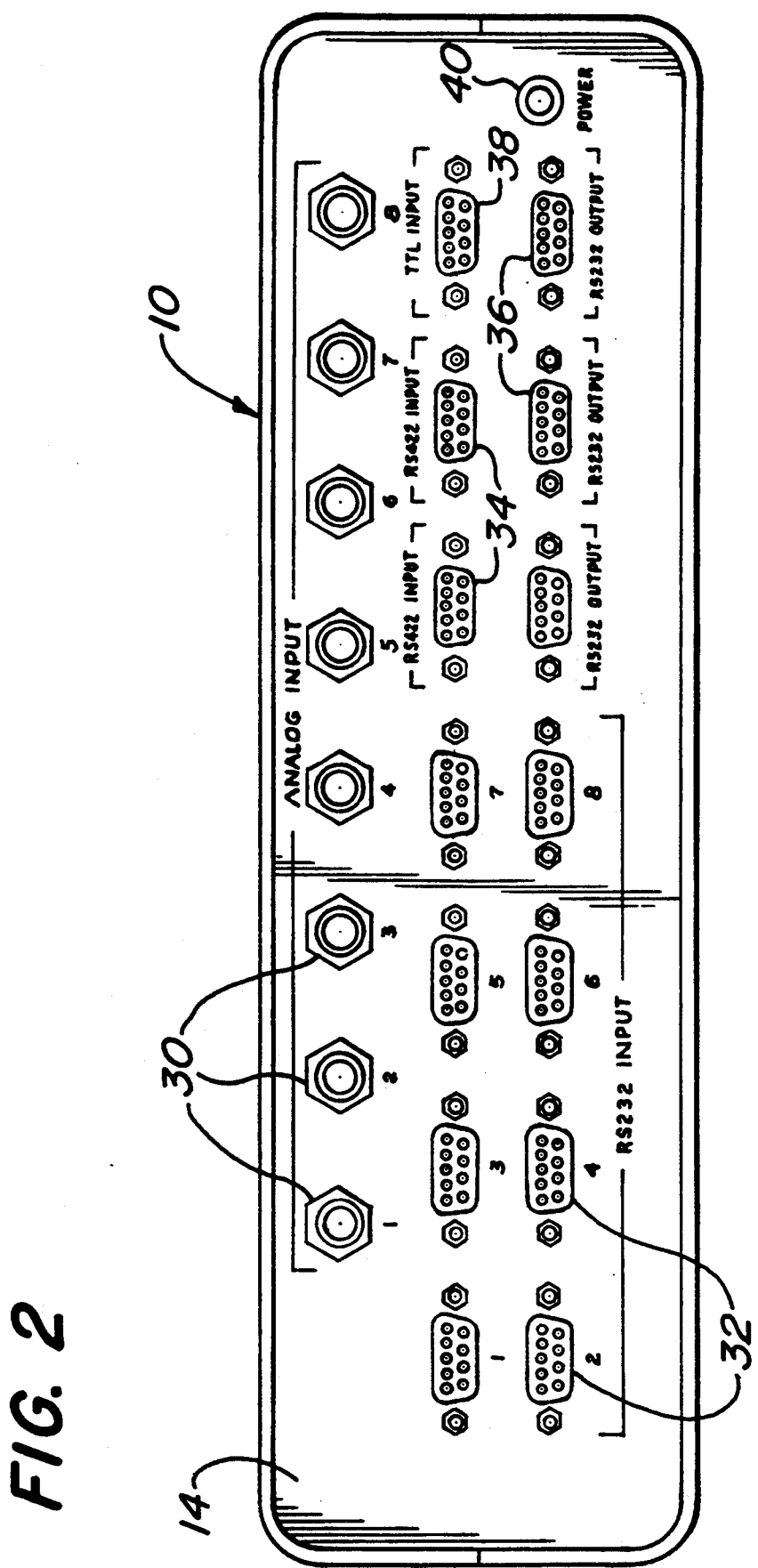
FIG. 2 is an elevation view of the front panel of the apparatus shown in FIG. 1 illustrating the various inputs and outputs utilized in connection with various data sources, such as patient monitors and other data sources.

The front panel 14 of the housing of apparatus 10 is shown in FIG. 2. There is shown on front panel 14 eight analog inputs 30 and eight RS232 inputs 32. In the lower right there is also shown two RS422 inputs 34 and three RS232 outputs 36. There is also a TTL input 38 and a power indicator 40.

Although a presently preferred embodiment of the apparatus of the present invention is illustrated in FIGS. 1 and 2, it is understood that various other arrangements may be utilized. Various types of housing arrangements may be utilized. The parallel printer ports may be mounted on the front panel, the top of the housing or the sides of the housing. With suitable leg arrangements, the parallel printer ports could even be mounted on the bottom of the housing. Similarly, the arrangement of the inputs and outputs for the data sources 30, 32, 34, 36 and 38 may be positioned anywhere on the housing, and are not in any way limited to being positioned on the front panel. Various arrangements of the other structure shown may be utilized as will be apparent to those skilled in the art. Further, as will be apparent to those skilled in the art, various choices as to the number of inputs and outputs may be made within the scope of the present invention.

Figure 3:
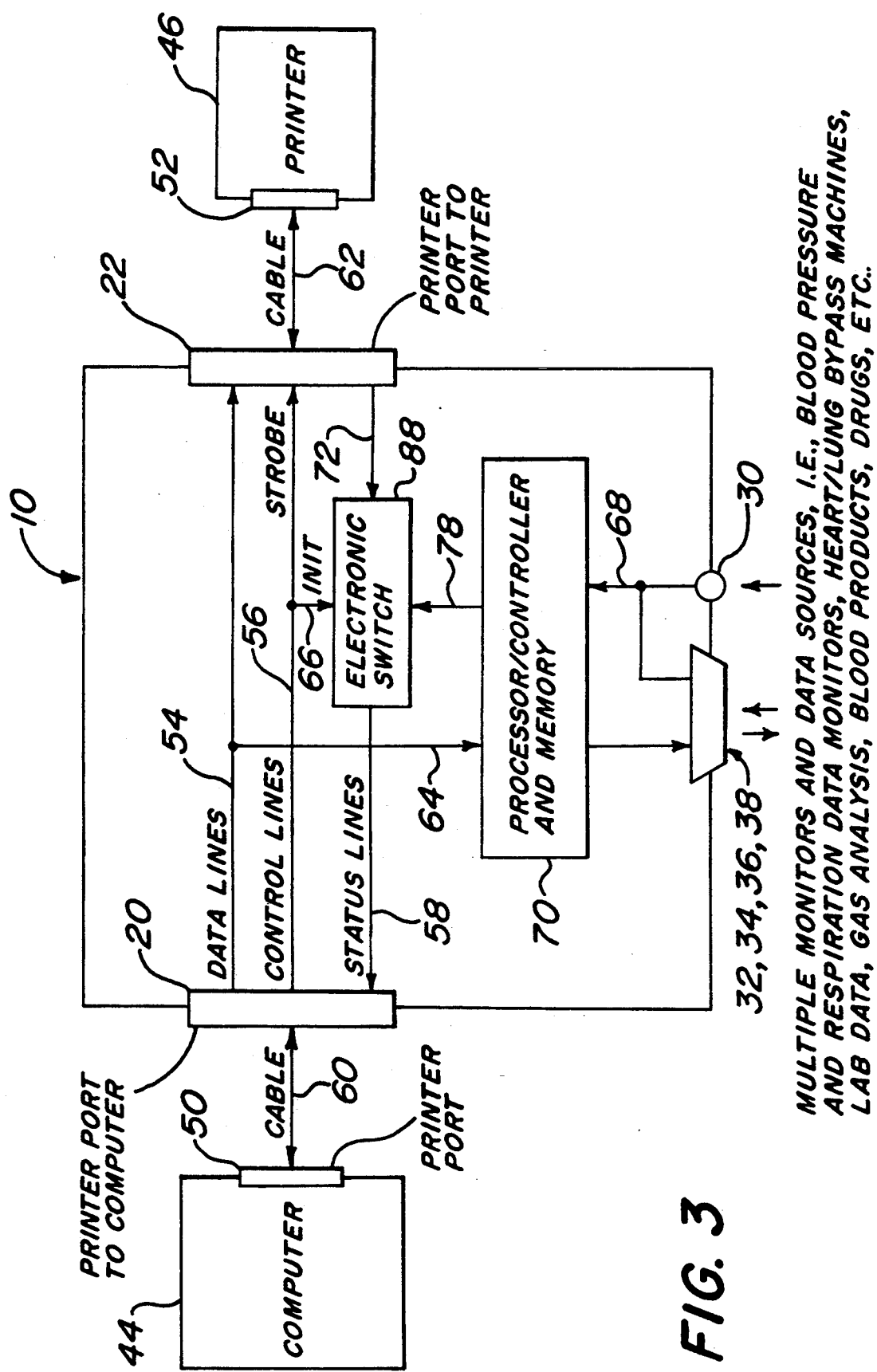
FIG. 3 is an overall conceptual schematic block diagram of the apparatus of the present invention.

Referring now to FIG. 3, there is shown a schematic block diagram of the apparatus 10 of the present invention as connected to a computer 44 and a printer 46. Computer 44 is provided with a standard parallel printer port 50. Parallel printer port 50 is connected to parallel printer port 20 of apparatus 10 via a cable 60. Computer 44 may be any one of various suitable computers capable to run a program to monitor, store in memory, display on demand, graph and display various patient values as requested from time to time by an anesthesiologist or other person monitoring the anesthetization of the patient.

Printer 46 may be any standard suitable printer utilized in connection with computers, and particularly, in a preferred embodiment, printer 46 is a laser printer. Printer 46 is provided with a parallel printer port 52 which is connected via cable 62 to parallel printer port 22 of apparatus 10. Within the printer ports 20, 22, 50 and 52, as well as cables 60 and 62, there are lines which are dedicated to carrying three types of data, namely data lines 54, control lines 56 and status lines 58. Data lines 54 are normally utilized to send text to the printer to be printed. Control lines 56 are normally utilized to control printer operation and status lines 58 are normally utilized to send data, as to status of the printer, etc, back to the computer.

In the present invention, data from data lines 54 is fed via line 64 to processor/controller and memory circuitry 70. One of the control lines 56 may be referred to as a strobe line, and is the line which carries the strobe signal to the printer. When the strobe signals are present, the printer is enabled to print data coming in on data lines 54. In the absence of strobe signals, the data from data lines 54, via lines 64, will be applied to processor/controller and memory circuitry 70 and ignored by the printer. This data from data lines 54 is processed by the processor, controller and memory circuitry 70 and is utilized to provide control to the processor/controller and memory circuitry 70 as well as control signals to data sources via the RS232 outputs 36 as may be needed. In other words, processor/controller and memory circuitry 70 may generate a request to be sent to a hospital laboratory for results on a laboratory analysis run on a patient specimen, i.e. blood. As illustrated in FIG. 3, some of the data sources connected via the inputs 30, 32, 34 and outputs 36 may be patient monitors, such as blood pressure and respiration data monitors, heart/lung bypass machines, laboratory data results, gas analysis, blood products analysis, drugs utilized and to be utilized.

Data from the RS232 inputs, the TTL input and the RS422 inputs as well as the analog inputs 30 are fed via line 68 to processor/controller and memory 70. After appropriate processing, such as multiplexing of the analog signals, converting them to digital signals and storing them until requested by the computer, the digital signals are also processed and stored until called for by the computer.

The processed data from the data sources in processor/controller and memory 70 is fed via line 78 to electronic switch 88 which is enabled to transmit data back to the computer via status lines 58 when an INIT signal is present on control line 66, which is one of the control lines 56. Electronic switch 88 allows transmission of status information from the printer via line 72 when the printer is enabled by the absence of the INIT signal.

Figure 4:
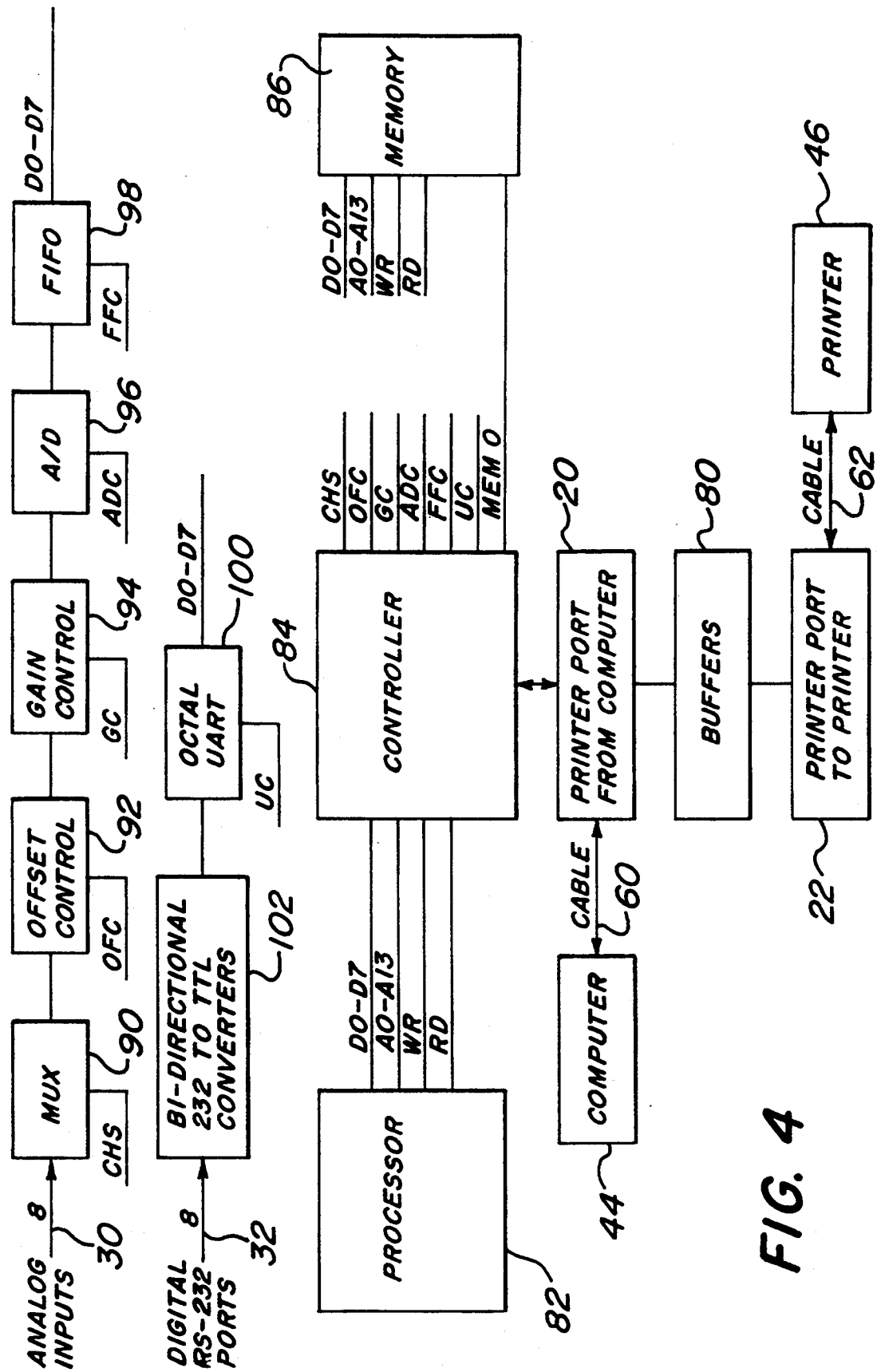
FIG. 4 is a more detailed schematic block diagram of the apparatus of the present invention.

Referring now to FIG. 4, there is shown a more detailed schematic block diagram of the circuitry of apparatus 10. In FIG. 4, lines having the same designation are connected together for example the eight data lines D0–D7 are electrically connected together. The channel select lines CHS are electrically connected together. One of the components of buffers 80 is electronic switch 88 discussed with respect to FIG. 3.

As described generally with respect to FIG. 3, processor 82 receives information from computer 44 via data lines D0–D7. For example, one type of information received by processor 82 from computer 44 is identification as to which monitors are connected to which ones of the analog inputs 30 and the digital ports 32, 34, 36 and 38. The processor 82, particularly in conjunction with controller 84 generates address signals A0–A13 for the storage of data in memory 86. Processor 82 also generates write (WR) and read (RD) commands to control writing in and reading from memory 86. Processor 82 may be any suitable processor, but in a presently preferred embodiment, processor 82 may be an ADSP–2105 commercially available from Analog Devices, One Technology Way, Norwood, MA 02062. Controller 84 may be any one of various suitable controllers, but in a presently preferred embodiment, controller 84 may be an XC3030–70 commercially available from Xilinx, 2100 Logic Drive, San Jose, CA 95124.

Analog data received on analog inputs 30 is multiplexed in multiplexor 90. The sequential channel selection to control proper timing and multiplexing is provided by controller 84 in response to outputs from processor 82 on the signal line labeled CHS. The output of multiplexor 90 is fed to an offset control or bias circuit 92. The amount of offset control is controlled by the output labeled OFC from the controller. The output of the offset control circuit 92 is fed to gain control circuit 94 which is controlled by a gain control signal GC also supplied by controller 84. The output of the gain control circuit 94 is applied to an analog to digital converter 96. The output of the analog to digital converter 96 is fed to a first in first out memory circuit 98 under the control of the FFC signal from the controller. The output of the first in first out memory circuit 98 is stored in memory 86 in conjunction with the appropriate address information provided by the processor 82 and controller 84. This information is then provided to the computer on demand on regular intervals. Typically, in a preferred embodiment, all of the data from memory 86, including both the data from the digital inputs and the analog inputs, is transferred to computer 44 every ten seconds.

The data on the digital RS232 ports 32 is processed by a bi-directional RS232 to TTL converter circuit 102. In other words, circuit 102 converts data which may be in the form of bi-directional signals to the computer format of data which is unidirectional digital pulses typically from zero to five (5) volts. Circuit 102 is utilized to convert data going both ways, that is RS232 signals to TTL signals utilizable by the computer and TTL signals utilizable by the computer to RS232 type signals which may be utilized by various monitors.

Bi-directional converter 102 is connected to an octal UART (universal asynchronous receiver-transmitter) circuit 100. UART circuit 100 processes eight bit serial data from the RS232 inputs and converts it into parallel data and vice versa. In other words UART 100 converts data from serial to parallel form in going from the monitors to the computer and converts parallel data to serial data to send signals to the monitors. Octal UART circuit 100 may be any suitable bi-directional converter circuitry, but in a presently preferred embodiment, this circuit is a SCC2698BC1A84 commercially available from Signetics, Phillips Components, 8111 East Arques Avenue, Sunnyvale, CA 94088.

The present invention may be embodied in other specific forms without departing from the spirit or essential attributes thereof and, accordingly, reference should be made to the appended claims, rather than to the foregoing specification as indicating the scope of the invention.

I claim:

1. Apparatus, comprising:
   an input/output controller to be used in connection with the anesthetization of a patient for inputting data from analog and digital patient sensory monitors and from other digital sources containing information relating to a patient's anesthetization to a computer utilized to monitor said patient's vital signs and other data;
   a plurality of connectors for receiving analog and digital data relating to the anesthetization of the patient;
   means for connecting to a parallel printer port of a computer;
   means for connecting to a parallel printer port of a printer; and
   means responsive to signals generated by said computer for selectively enabling said computer to print data or enabling said computer to receive data relating to the patient's anesthetization from a plurality of data sources via said plurality of connectors for receiving analog and digital data, storing said data in a memory at addresses corresponding to the source connected to each of said plurality of connectors and sending the data to said computer in response to said signals generated by said computer.

2. Apparatus in accordance with claim 1 wherein said means for connecting to a parallel printer port of a computer includes a parallel port mounted on said apparatus and connected to said parallel port of said computer by a cable.

3. Apparatus in accordance with claim 1 wherein said means for connecting to a parallel printer port of a printer includes a parallel port mounted on said apparatus and connected to said parallel port of said printer by a cable.

4. Apparatus in accordance with claim 1 wherein said means responsive to signals generated by said computer generates a signal for transmission to at least one of said plurality of data sources.

5. Apparatus in accordance with claim 4 wherein said one of said plurality of data sources is a sensory patient monitor.

6. Apparatus, comprising:
   an input/output controller for use in connection with the anesthetization of a patient functioning as a data interface between a computer and a plurality of patient monitors and other data sources;
   means for connecting to a parallel printer port of said computer;
   means for connecting to a plurality of analog and digital patient sensory monitors for sensing the condition of an anesthetized patient;
   means responsive to signals generated by said computer, said means including a processor, memory and signal processing means, said signal processing means including circuitry for multiplexing a plurality of analog signals received from said patient monitors and converting them to digital signals for storage in said memory, said processor, in response to information from the computer as to which patient sensory monitors are connected to selected connecting means, controlling the storage of said digital signals containing information relating to a patient's anesthetization memory at appropriate addresses, said processor retrieving selected stored signals containing information relating to a patient's anesthetization from memory as called for by said computer and enabling transmission of said signals to said computer.

7. Apparatus in accordance with claim 6 wherein said signal processing circuitry includes circuitry for converting RS232 type signals to TTL signals, said processor controls the storage of said signals in memory and transmits selected signals to said computer in response to computer requests.

8. Apparatus in accordance with claim 6 wherein said processor receives control signals via data lines from said means connected to said parallel printer port for generating a signal for transmission to at least one patient sensory monitor for sensing the condition of an anesthetized patient.

9. Apparatus in accordance with claim 6 including means for connecting to a parallel printer port of a printer to enable data from said computer relating to the anesthetized patient to be transmitted to a printer for printing in response to a strobe pulse disabling the processing of data by said processor.

10. Apparatus in accordance with claim 9 including means for controlling data flow whereby said printer may be enabled by a strobe pulse for printing and disabled by the absence of a strobe pulse whereby data on the data lines is utilized to control said processor.

11. Apparatus, comprising:
a housing containing electronic circuitry for enabling a computer to receive data relating to anesthetization of a patient from a plurality of analog and digital sources, and for selectively sending data to said digital data sources and to a printer, said computer being adapted to process, display and send data relating to a patient undergoing a surgical procedure including information relating to the anesthetization of the patient;
a parallel printer port mounted on said housing for connection to a printer;
a parallel port mounted on said housing for connection to said computer;
a plurality of analog input connections adapted to receive data sent from patient sensory monitors mounted on said housing for connection to a plurality of patient sensory monitors;
a plurality of digital input/output connections mounted on said housing for connection to patient sensory monitors and other sources/recipients of data relating to the patient undergoing surgery;
signal processing means mounted in said housing, said signal processing means including means for multiplexing and converting analog signals received via said plurality of analog input connections to digital signals and means for bi-directionally converting digital signals to digital signals suitable for use by said computer and said other sources/recipients of data relating to the patient undergoing surgery; and
processor/control circuitry for controlling said signal processing means and digitally storing in a memory received and processed analog and digital signals, said processor/control circuitry controlling the sending of digitally stored signals from said memory to said computer upon demand from said computer, sending data and requests for data from said computer to said other sources/recipients of data relating to the patient undergoing surgery and sending data from said computer to said printer via said parallel printer port.

12. Apparatus in accordance with claim 11, wherein said means for bi-directionally converting digital signals suitable for use by said computer and said other sources/recipients of data relating to the patient undergoing surgery includes circuitry for bi-directionally converting RS232 type signals to TTL signals.

13. Apparatus in accordance with claim 11 wherein said processor/control circuitry includes electronic switch means enabled by a signal from the computer to send data back to said computer via the status lines normally utilized to provide data to said computer as to the status of said printer.

* * * * *